United States Patent [19]
Minoz

[11] Patent Number: 6,115,622
[45] Date of Patent: Sep. 5, 2000

[54] AMBULATORY RECORDER HAVING ENHANCED SAMPLING TECHNIQUE

[75] Inventor: Alain Minoz, Bromma, Sweden

[73] Assignee: Medtronic, Inc., Minneapolis, Minn.

[21] Appl. No.: 09/130,149

[22] Filed: Aug. 6, 1998

[51] Int. Cl.$^7$ ..................................................... A61B 5/00
[52] U.S. Cl. ........................ 600/361; 600/300; 600/301; 600/309; 600/508
[58] Field of Search ..................................... 600/300, 301, 600/309, 361, 508, 509; 128/920, 921, 903

[56] References Cited

U.S. PATENT DOCUMENTS

| | | |
|---|---|---|
| D. 396,037 | 7/1998 | Cappa et al. . |
| 3,898,984 | 8/1975 | Mandel et al. . |
| 3,941,137 | 3/1976 | Vredenbregt et al. . |
| 4,003,379 | 1/1977 | Ellinwood, Jr. . |
| 4,082,084 | 4/1978 | Lipscher . |
| 4,129,125 | 12/1978 | Lester et al. . |
| 4,183,354 | 1/1980 | Sibley et al. . |
| 4,198,963 | 4/1980 | Barkalow et al. . |
| 4,333,475 | 6/1982 | Moreno et al. . |
| 4,353,375 | 10/1982 | Colburn et al. . |
| 4,365,636 | 12/1982 | Barker . |
| 4,370,983 | 2/1983 | Lichtenstein . |
| 4,464,172 | 8/1984 | Lichtenstein . |
| 4,503,859 | 3/1985 | Petty et al. . |
| 4,529,401 | 7/1985 | Leslie et al. . |
| 4,531,527 | 7/1985 | Reinhold, Jr. et al. . |
| 4,592,018 | 5/1986 | Wiegman . |
| 4,628,928 | 12/1986 | Lowell . |
| 4,632,119 | 12/1986 | Reichstein . |
| 4,667,682 | 5/1987 | Ihlenfeld, III . |
| 4,684,367 | 8/1987 | Schaffer et al. . |
| 4,715,385 | 12/1987 | Cudahy et al. . |
| 4,748,562 | 5/1988 | Miller et al. . |
| 4,771,772 | 9/1988 | DeWitt . |
| 4,774,956 | 10/1988 | Kruse et al. . |
| 4,794,934 | 1/1989 | Motoyama et al. . |
| 4,895,161 | 1/1990 | Cudahy et al. . |
| 4,900,305 | 2/1990 | Smith et al. . |
| 4,917,092 | 4/1990 | Todd et al. . |
| 4,974,599 | 12/1990 | Suzuki . |
| 5,002,062 | 3/1991 | Suzuki . |
| 5,007,427 | 4/1991 | Suzuki et al. . |
| 5,010,888 | 4/1991 | Jadvar et al. . |
| 5,012,411 | 4/1991 | Policastro et al. . |
| 5,016,636 | 5/1991 | Kulakowski . |
| 5,042,481 | 8/1991 | Suziki et al. . |
| 5,072,458 | 12/1991 | Suzuki . |
| 5,086,778 | 2/1992 | Mueller et al. . |
| 5,107,835 | 4/1992 | Thomas . |
| 5,111,396 | 5/1992 | Mills et al. . |
| 5,111,818 | 5/1992 | Suzuki et al. . |
| 5,113,869 | 5/1992 | Nappholz et al. . |
| 5,117,827 | 6/1992 | Stuebe et al. . |
| 5,131,816 | 7/1992 | Brown et al. . |
| 5,158,083 | 10/1992 | Sacristan et al. . |
| 5,188,104 | 2/1993 | Wernicke et al. . |
| 5,213,568 | 5/1993 | Lattin et al. . |
| 5,222,503 | 6/1993 | Ives et al. . |
| 5,224,485 | 7/1993 | Powers et al. . |

(List continued on next page.)

FOREIGN PATENT DOCUMENTS 0 356 603  9/1988  Sweden .

*Primary Examiner*—Eric F. Winakur
*Attorney, Agent, or Firm*—Thomas F. Woods; Michael J. Jaro; Harold Patton

[57] ABSTRACT

An ambulatory recorder which features an enhance technique for sampling. The ambulatory recorder has a programmable number of channels, each channel having a programmable sampling frequency rate. The multi channel ambulatory recorder is fashioned so as to sample and records data only from each channel as desired at the frequency as desired. The recorder examines the frequencies on the channels for which data is to be sampled and recorded, and selects a common tick frequency for the microprocessor to awaken, sample and sleep again. Moreover, the microprocessor is directed to only sample at each tick on each channels as needed reducing the amount of required memory and shortening the time it is consuming power.

13 Claims, 8 Drawing Sheets

U.S. PATENT DOCUMENTS

| | | |
|---|---|---|
| 5,226,431 | 7/1993 | Bible et al. . |
| 5,228,450 | 7/1993 | Sellers . |
| 5,238,001 | 8/1993 | Gallant et al. . |
| 5,261,401 | 11/1993 | Baker et al. . |
| 5,263,491 | 11/1993 | Thornton . |
| 5,273,033 | 12/1993 | Hoffman . |
| 5,292,344 | 3/1994 | Douglas . |
| 5,305,202 | 4/1994 | Gallant et al. . |
| 5,305,761 | 4/1994 | Byrne et al. . |
| 5,307,263 | 4/1994 | Brown . |
| 5,309,920 | 5/1994 | Gallant et al. . |
| 5,338,157 | 8/1994 | Blomquist . |
| 5,341,291 | 8/1994 | Roizen et al. . |
| 5,343,870 | 9/1994 | Gallant et al. . |
| 5,355,892 | 10/1994 | Saltzstein . |
| 5,368,562 | 11/1994 | Blomquist et al. . |
| 5,381,351 | 1/1995 | Kwong et al. . |
| 5,388,587 | 2/1995 | Knutsson et al. . |
| 5,411,022 | 5/1995 | McCue et al. . |
| 5,429,602 | 7/1995 | Hauser . |
| 5,431,634 | 7/1995 | Brown . |
| 5,432,698 | 7/1995 | Fujita . |
| 5,438,985 | 8/1995 | Essen-Moller . |
| 5,479,019 | 12/1995 | Gross . |
| 5,479,935 | 1/1996 | Essen-Moller . |
| 5,507,904 | 4/1996 | Fisher et al. . |
| 5,526,809 | 6/1996 | Fiddian-Green . |
| 5,545,183 | 8/1996 | Altman . |
| 5,607,460 | 3/1997 | Kroll . |
| 5,645,068 | 7/1997 | Mezack et al. . |
| 5,657,759 | 8/1997 | Essen-Moller . |
| 5,701,894 | 12/1997 | Cherry et al. . |
| 5,704,368 | 1/1998 | Asano et al. . |
| 5,704,890 | 1/1998 | Bliss et al. . |
| 5,749,907 | 5/1998 | Mann .- |

FIGURE 3A
Channel 1 sampled at 1/4 Hz (every 4000ms)
Channel 2 sampled at 1 Hz (every 1000ms)
Channel 3 sampled at 4 Hz (every 250ms)
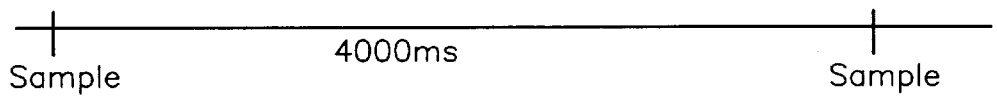
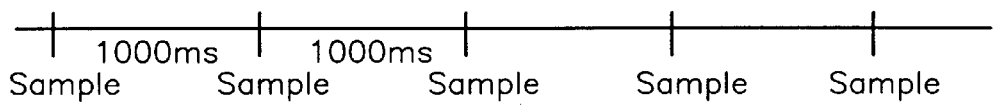
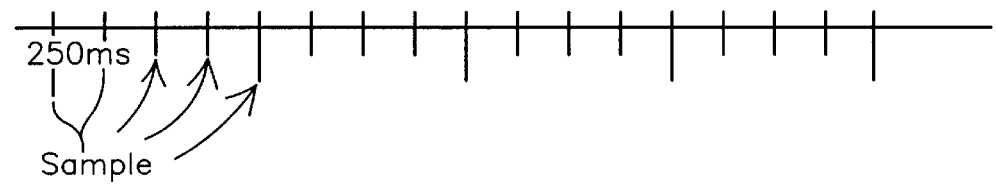
FIGURE 3B
| Channel | Nb of samples |
|---|---|
| 1 | 16 |
| 2 | 16 |
| 3 | 16 |
| Total | 48 data points |
FIGURE 3C
| Channel | Nb of samples |
|---|---|
| 1 | 1 |
| 2 | 2 |
| 3 | 16 |
| Total | 19 data points |

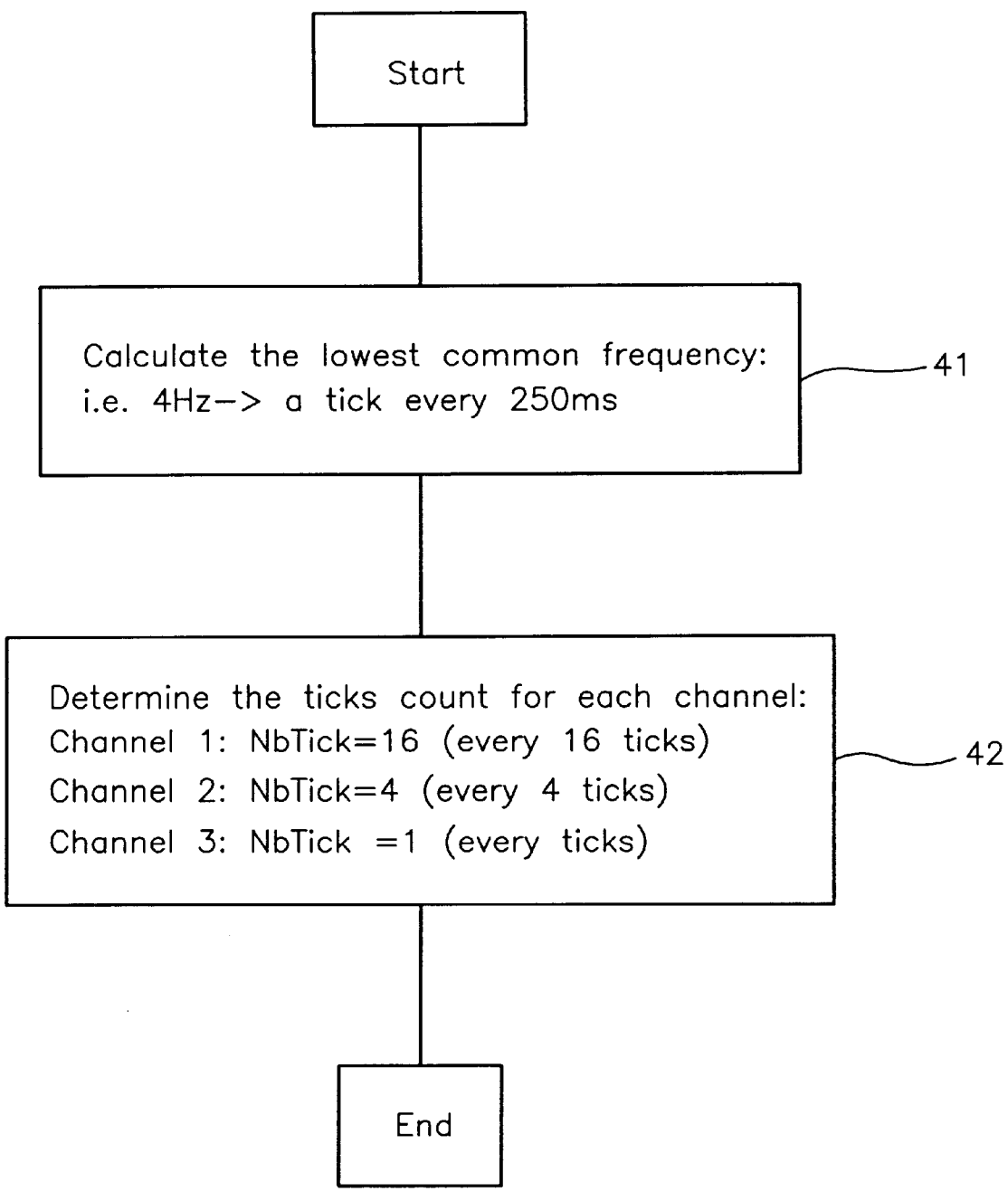

FIGURE 6

| Tick | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| Tch1 | 0 | 15 | 14 | 13 | 12 | 11 | 10 | 9 | 8 | 7 | 6 | 5 | 4 | 3 | 2 | 1 | 0 |
| Tch2 | 0 | 3 | 2 | 1 | 0 | 3 | 2 | 1 | 0 | 3 | 2 | 1 | 0 | 3 | 2 | 1 | 0 |
| Tch3 | 0 | 0 | 0 | 0 | 0 | 0 | 0 | 0 | 0 | 0 | 0 | 0 | 0 | 0 | 0 | 0 | 0 |

0 ⇒ Sample

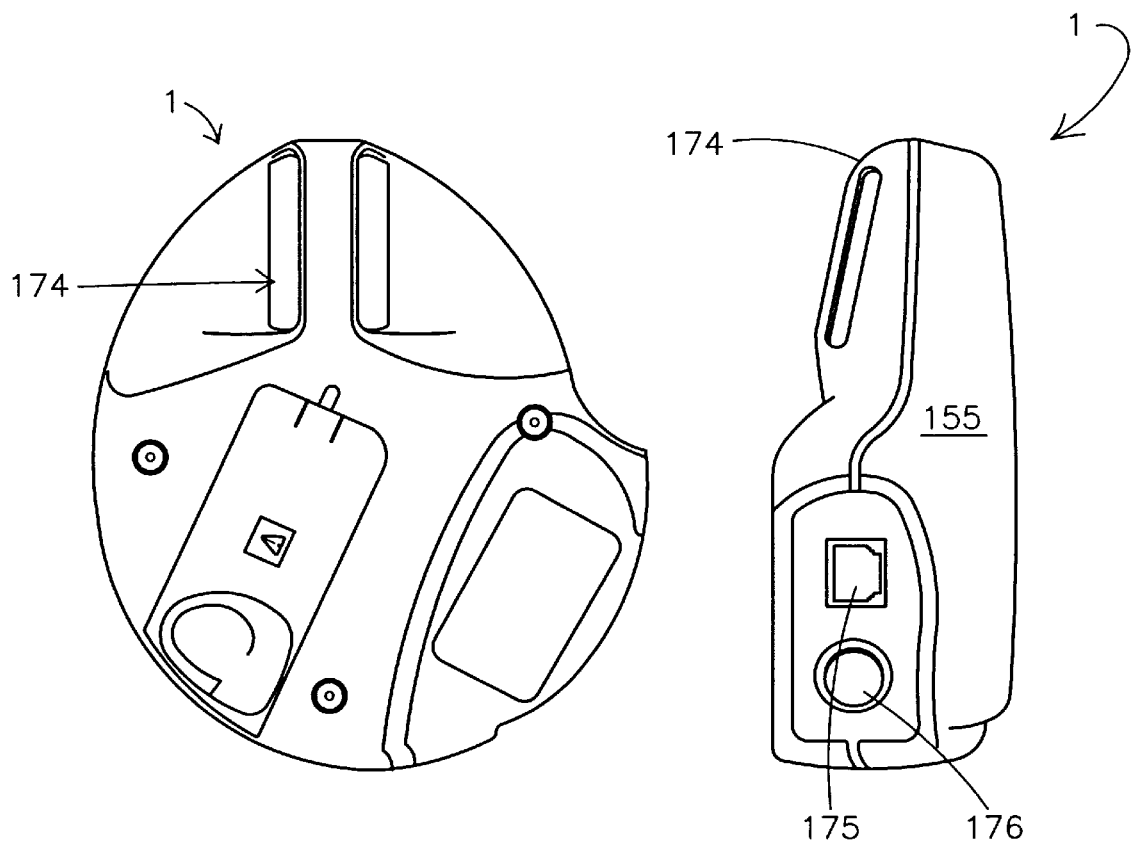
FIGURE 8  FIGURE 9

AMBULATORY RECORDER HAVING ENHANCED SAMPLING TECHNIQUE

FIELD OF THE INVENTION

The present invention relates to an ambulatory recorder and particularly to an ambulatory recorder which features an enhanced technique for sampling medical or physiological data.

Ambulatory recording and recorders are widely used to collect medical data. Such devices include the Digitrapper Mk III™ ambulatory recorder from Synectics Medical AB, the GastroScan II™ from Medical Instruments Corporation, and the SuperLogger™ from Sandhill Scientific. These types of devices make it possible for patients to remain at home, or at least to be ambulatory in a hospital setting while physiological data is recorded. Typically the devices comprise a lightweight recorder in which the desired physiological data signals are temporarily stored and later downloaded for future analysis.

Many types of physiological data may be recorded, including ECG (Electrocardiogram) data, EEG (Electroencephalogram) data or pH and pressure data (Motility) in the gastrointestinal tract. Preferably such a recorder should be able to record among a programmable number of channels at a variety of programmable frequencies.

Among the problems with current recorders, however, is that of energy usage. Such recorders, because they are ambulatory, are battery powered.

Battery operated devices, however, operate under many constraints. Because they have only a limited amount of energy available for use, they often must be very simple in design and execution, while also having limited memory. In regards to multi channel ambulatory recorders, such as GI recorders, these limitations are further felt through the requirement that multiple channels be recorded. Moreover, these multiple channels often are recorded using differing sampling frequencies.

Past methods of dealing with the need to sample multiple channels at multiple sampling frequencies with limited memory and power have been less than satisfactory.

One method used was to sample across all channels at the highest required frequency. This method, however, used more energy than was necessary because sampling was done on all the channels, including those in which such high sampling rates were not required. This method also resulted in excess data being acquired, which drained limited memory resources.

Another method used was to sample across all channels at the highest required frequency but drop data along specific channels which was not desired. While this method addressed the excess memory usage of the prior art method described above, it still used more energy than was necessary because sampling of undesired channels still occurred.

Thus there exists a need for a battery operated ambulatory device which can sample and record data along multiple channels, but which only samples and records along each of the desired channels at the required times.

SUMMARY

An ambulatory recorder which features an enhance technique for sampling is described. The ambulatory recorder has a programmable number of channels, each channel having a programmable sampling frequency rate. The ambulatory recorder is fashioned so as to sample and record data only from desired channels at desire frequencies. The recorder examines the frequencies on the channels for which data is to be sampled and recorded, and selects a common sampling frequency at which the microprocessor awakens samples and sleeps. Moreover, the microprocessor is directed to only sample those channels which are desired reducing the amount of required memory and shortening the amount of time the recorder consumes power.

BRIEF DESCRIPTION OF THE DRAWINGS

FIG. 3 illustrates one difficulty with the programmable multi-channel sampling environment at programmable multiple frequencies of the present invention.

FIG. 4 illustrates the device operation.

FIG. 6 depicts the value of the respective channels Tch1 to Tch3 over a series of microprocessor tick cycles.

FIG. 8 is a back view of the recorder.

FIG. 9 is a side view of the recorder.

The FIGS. are not necessarily to scale.

DETAILED DESCRIPTION OF THE DRAWINGS

Figure 1A:
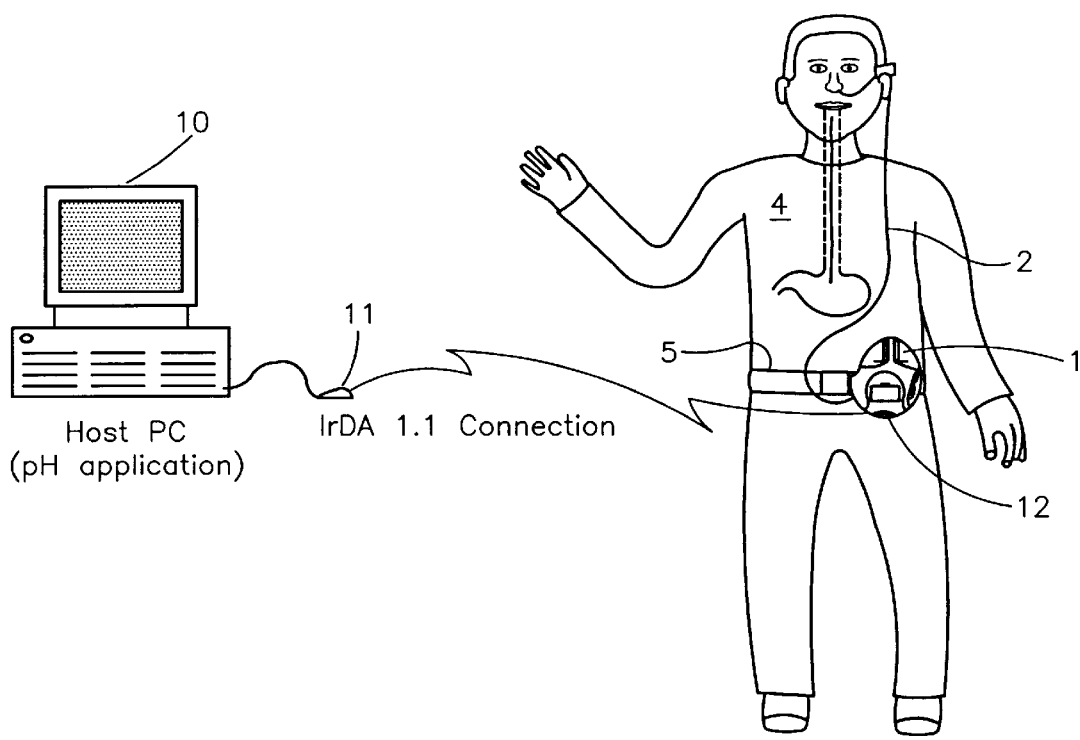
FIG. 1A depicts an ambulatory recorder of the present invention.

FIG. 1A depicts an ambulatory recorder of the present invention. As seen, ambulatory recorder 1 of the present invention may be carried by a patient. In the preferred embodiment, the recorder may be either carried using a mounting attached to the back of the recorder enclosure which fastens to a patient's belt 5, or the same mounting may be coupled to a shoulder harness (not shown). As seen, recorder is coupled to the patient 4 through one or more sensing catheters 2. Sensing catheters may be positioned in any area of the patient's body from which data is to be sensed, including the esophagus, as depicted in FIG. 1A. It should be noted that, the ambulatory recorder of the present invention may be used to collect many or various types of data including gastrointestinal data such as pH and pressure data, neurological data, and neuromuscular, EEG or EMG data.

Among the various sensing catheters which may be coupled to the device are manometry catheters and pH testing catheters, including the Synectics Medical AB, Stockholm, Sweden Model G 91-9 series of Multi use pH catheters; Synectics Medical AB Model G 91-2 series of Multi use pH catheters with perfusion port; or the Zinectics Inc., Salt Lake City, Utah disposable 24 pH catheter Model series G91-6 or G 91-7. While a single catheter 2 is shown depicted in FIG. 1A, recorder 1 may further permit two separate sensors to be coupled to the device, as seen in FIG. 1B.

Figure 1B:
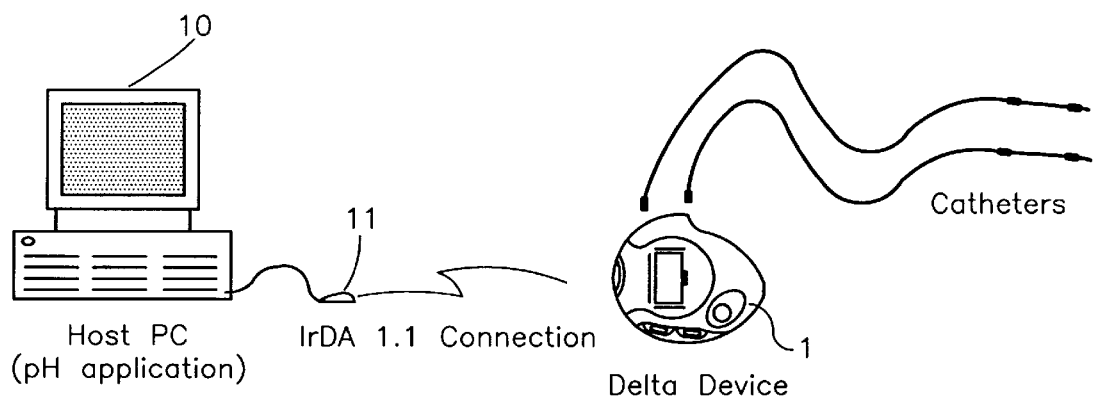
FIG. 1B illustrates a further manner in which the recorder 1 may also have an infra red data communication link made with a host PC.

As further seen in FIG. 1B, the recorder may also communicate with a host PC 10 via an infra red data link facility through an IrDA connection 11, such as for example, a JETEYE ESI-57680 device available from Extended Systems, Inc., Boise, Id., which establishes communication with recorder 1 using the infra Red Data Association 1.1 Connection Protocol. As seen, infra red data connection makes a link to infra red port 12 on recorder.

FIG. 1B illustrates a further manner in which recorder 1 may also establish an infra red data communication link with a host PC. In particular, the infra red data communication data recorder may be established when the recorder is not worn by the patient. As discussed in more detail below, one of the advantages of the present invention is that the infra red data components and recorder case permit such a link to be established when the device is worn as shown in FIG. 1A, or when, the device is removed from the patient and positioned in proximity to mouse 11.

Figure 2:
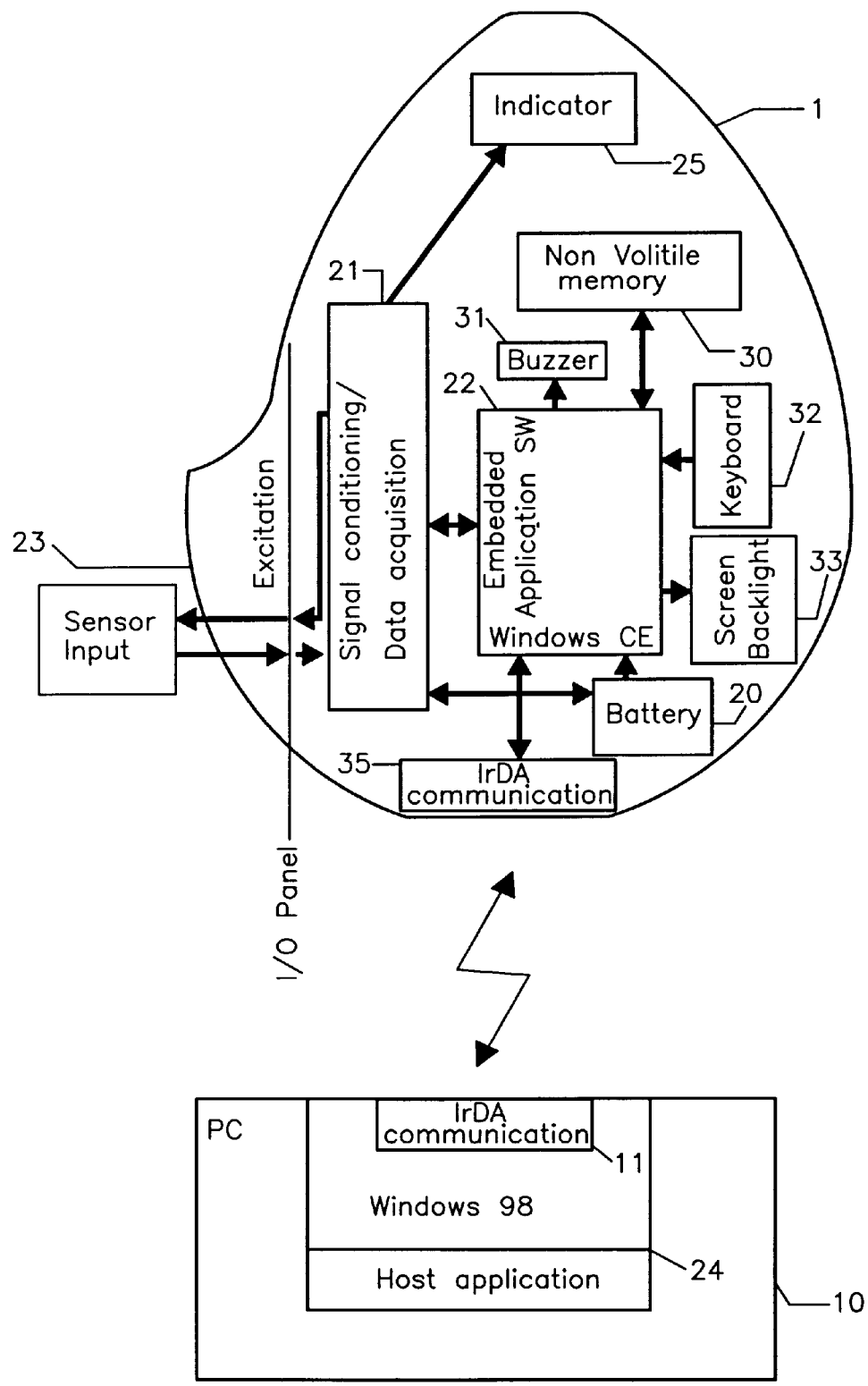
FIG. 2 is a block diagram of the data recording system shown in FIG. 1B.

FIG. 2 is a block diagram of the data recording system shown in FIG. 1B. As seen, recorder 1 features a battery 20 which is coupled to the signal conditioning/data acquisition block driven by a real time processor 21. Battery 20 powers non-real time processor 22 that runs the application. As disclosed in more detail below, real time processor 21 is a low power processor which is used to sample data which is received from sensor input 23 by a sensor attached thereto (not shown in FIG. 2).

Sampling is achieved through the signal conditioning providing an excitation to the sensor coupled to sensor input 23. Such excitation voltage is often used to power and, thus, permit sensing to occur in a variety of different types of sensors, including pressure sensors, as is well known in the art. The sampling and sensing controls are provided by the real time processor 21. Real time processor also drives a LED indicator 25 to show the system is running even when the screen is off.

As further seen, this processor is coupled to second non-real time processor 22. Second processor 22 is provided primarily to perform those high processing operations associated with multitasking, graphical. In particular, second processor is primarily provided to operate a Windows CE operating system as well as one or more embedded applications, as depicted. As further seen, this processor is coupled to audible buzzer 31 as well as keyboard controls 32, a screen 33 and non-volatile memory 30. Non-volatile memory provides a long term memory for the device such that data can be recorded and preserved, even if power is lost In the preferred embodiment, keyboard controls processes a series of four push buttons, each of which provide one or more different types of system inputs, as provided by the Windows CE™ operating system, available from Microsoft Corporation, Redmond, Wash.

As further seen in this figure, recorder features an infra red port 35 to communicate with the host user interface, floating point calculation, Infra Red communication and long term memory storage PC. As depicted in FIG. 1B, the infra red connection permits recorder 1 to receive and exchange data with host PC 10. Host PC, as seen, includes both a Windows 98™ operating system available from Microsoft Corporation, Redmond, Wash., as well as one or more host applications. Host applications permit the diagnosis of the recorded values.

In a preferred embodiment of the present invention the real time processor 21 is a model PIC16LC67IC from Microchip Technology Inc., Chandler, Ariz.; non-real time processor 22 is a model ElanSC400IC from Advanced Micro Devices, Inc. Sunnyvale, Calif.; and non-volatile memory 30a model Minicard AMMCL004AWP from Advanced Micro Devices, Inc. Sunnyvale, Calif.

FIG. 3 illustrates one difficulty with the programmable multi-channel sampling environment of the present invention. Channel 1 could be programmed to be sampled every 4 seconds, while channel 2 could be programmed to be sampled every second and channel 3 once every 250 milliseconds. Thus, it is necessary that the processor sample at least one channel every 250 milliseconds. However, this amount of sampling is only necessary in respect of channel 3. If sampling at the same rate were to occur in respect of channel 2 and channel 1, then increased current drain would occur due to the needless provision of excitation voltage to the sensing catheter along channels 2 and 1, even though such data is not required. In addition, over sampling on channels 1 and 2 would result in data being stored memory which is not required. An example of this is seen in FIG. 3B, which shows that if channels 1, 2 and 3 were to be sampled at the shortest time interval over 4 seconds, channels 1, 2 and 3 would produce a total of 48 data points.

As discussed above, the present invention provides the means for minimizing the amount of unnecessary sampling that occurs. The present invention thus permits sampling to occur only on those channels at those frequencies desired. In the example given above this would mean channel 3 is, sampled once every 250 milliseconds, channel 2 is sampled once every second and channel 1 is sampled once every 4 seconds. Thus, as seen in FIG. 3C, the sampling method of the current invention yields only 19 data points to be collected over the same time period as compared to 48 data points illustrated in FIG. 3B (resulting in to 60% less memory being required.)

FIG. 4 illustrates the operation to set up the sampling procedure. As seen in block 41, the device examines the frequencies at which sampling is to occur for each channel and calculates the lowest common frequency (4 Hz in our example).

Next, at 42 the device sets respective numbers of tick counters for each channel and its associated sample rate. The Tick counter represents the number of ticks to wait before sampling a channel. A value of 1 means that the channel is to be sampled each tick, a value of 2 means a channel is to be sampled every 2 ticks, and so on.

Figure 5:
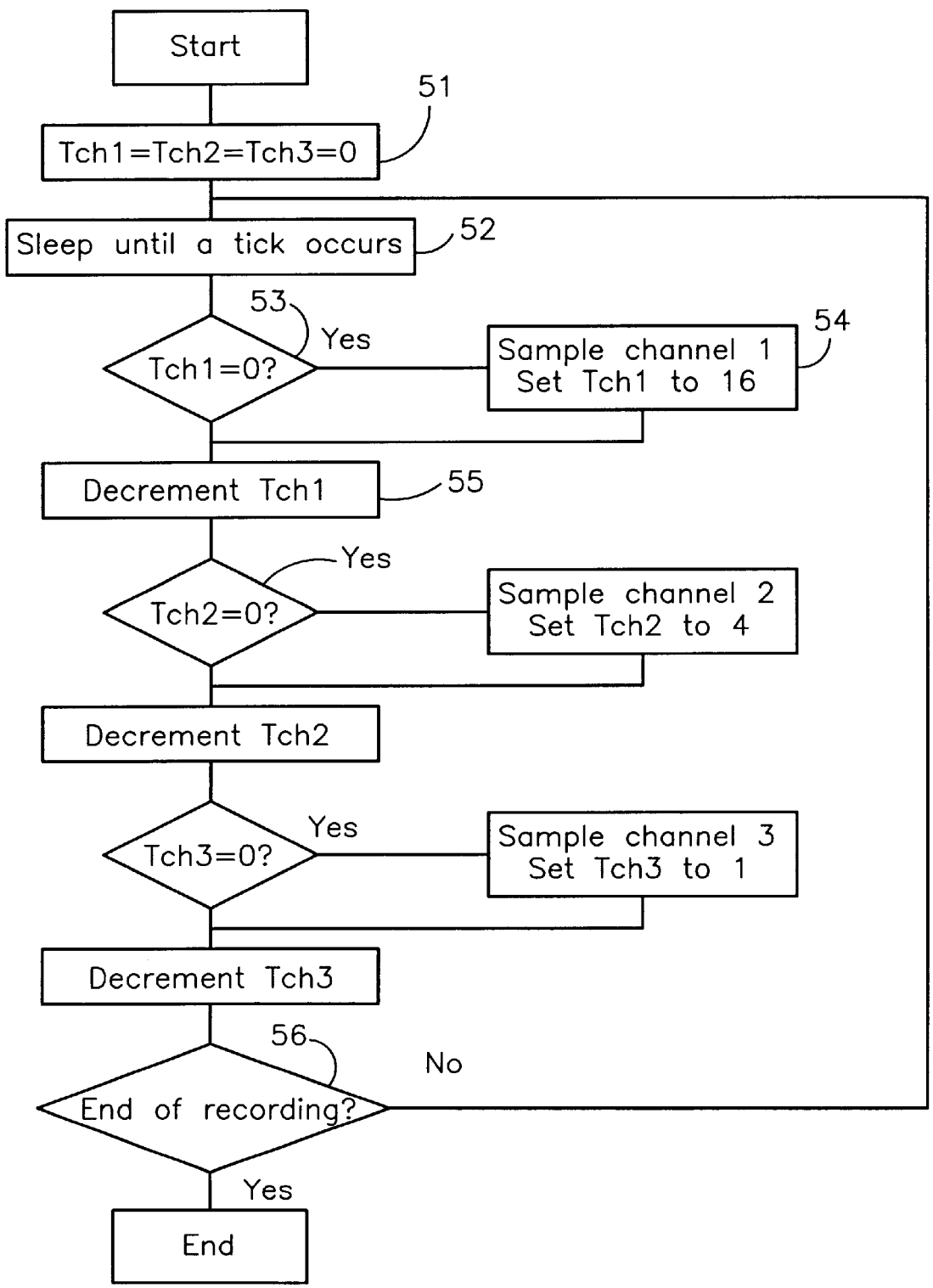
FIG. 5 is a flow chart depicting the operation using the tick counters through which sampling may be controlled.

FIG. 5 is a flow chart depicting using the tick counters and controlling sampling rates. In step 51, the device sets the variable tick counters for each channel to zero. It waits then until a tick occurs at 52 (the first tick occurs instantaneously). In block 53, Tch1 is examined to determine if so equal to zero. If it is, the microprocessor samples channel 1 in step 54 and the device thereafter sets Tch1 as NbTicks for channel 1 (16 in the example). If Tch1 is not equal to zero, sampling of that channel is skipped. In each case of branch 53, the device proceeds to block 55 and Tch1 is decremented. The same pattern (53, 54, 55) is repeated for each channel that have to be sampled. The device then checks if it is at the end of the sampling period in step 56. If it is not, it goes back to step 52 and waits for the next tick.

The result of such an operation may be seen in FIG. 6, which depicts the values of the respective channels Tch1 to Tch3 over a series of microprocessor tick cycles. As seen at tick 1, Tch1, Tch2 and Tch3 are all equal to zero, at which time sampling occurs across all channels. During tick cycle 2, Tch3 remains at zero and sampling occurs. For Tch1 and Tch2, however, the values are slightly decremented in units of one until they again reach zero—only at tick cycle 5 for channel 2 and cycle 17 for channel 1—. Thus, through such a counting mechanism sampling may be controlled such that channel 1 is sampled every sixteenth tick or time increment channel 2 is sampled every fourth tick or time increment, and channel 3 is sampled every tick or time increment. Thus, such a scheme permits sampling to only occur on each channel at a desired frequency or sample rate.

Figure 7:
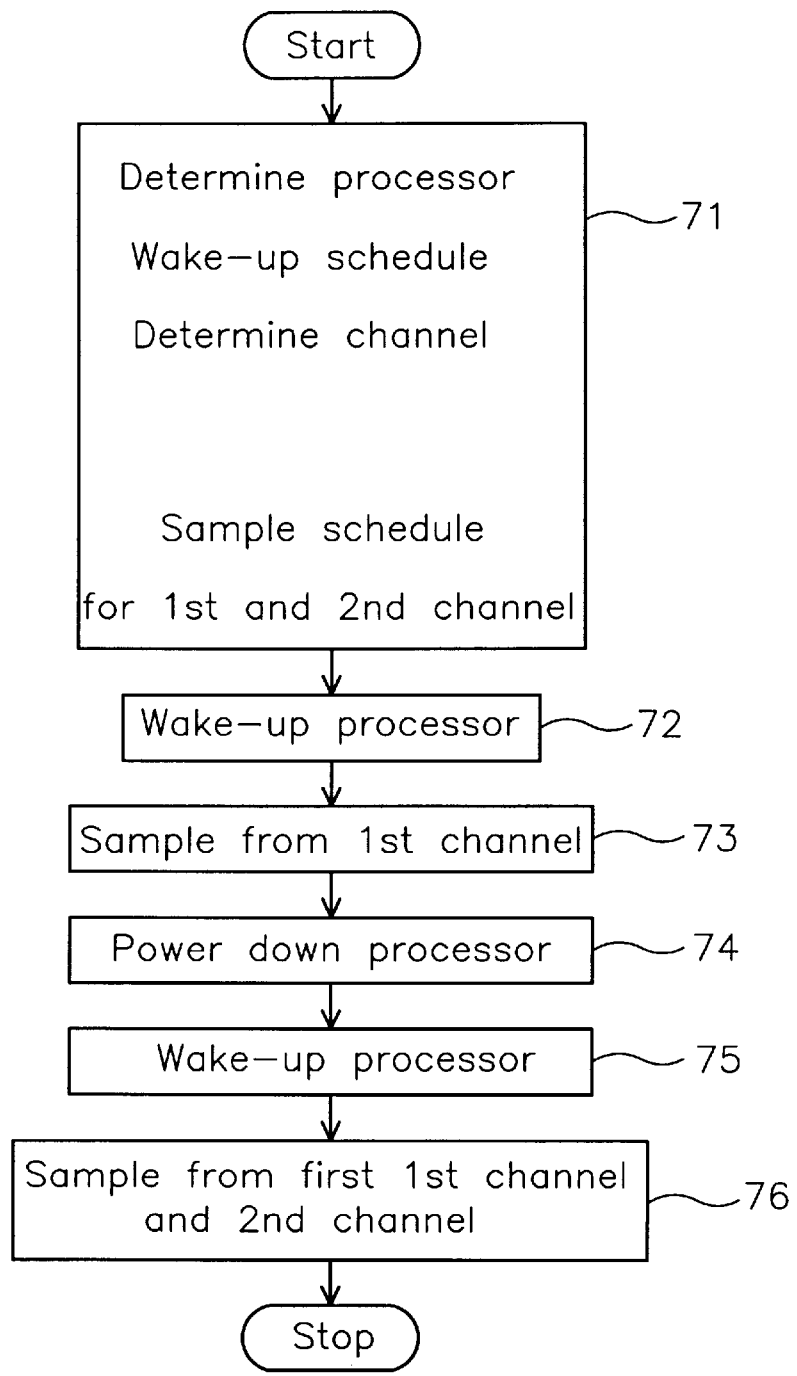
FIG. 7 depicts general steps used in the recorder to permit sampling across various channels across various frequencies.

FIG. 7 depicts general steps used in the recorder to permit sampling across various channels using different sample rates. As seen in block 71, the processor wakeup cycle is determined. This processor wake-up cycle is determined in a manner using the method depicted in FIGS. 4 and 5. In addition, the channel sampling cycle is determined for at least a first and a second channel. Thereafter, the device proceeds to block 72 at which time the processor is awakened to permit sampling to occur along the first channel as depicted at block 73. Thereafter, in block 74, the processor is powered down in order to save energy. The processor is again awakened at block 75. The device may thereafter provide sampling from the first channel as well as the second channel, as seen at block 76.

FIG. 8 is a back view of the recorder. As seen, recorder 1 features a belt loop 174 which may be used to mount the recorder to a patient using either the patient's belt or the shoulder strap.

FIG. 9 is a side view of recorder 1. As further seen in this view, housing 155 features a pair of sensor inputs 175 and 176. In the preferred embodiment, input 175 is configured to connect to a pH catheter while input 176 is configured to connect to a pressure measuring catheter.

Although various embodiments of the invention have been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. A method of conserving battery charge in a battery-powered ambulatory medical data recorder, the ambulatory data recorder comprising a plurality of data channels connected to a plurality of corresponding medical sensors, including a first medical data sensor connected to a first data channel and a second medical data sensor connected to a second data channel, the ambulatory data recorder further comprising a battery-powered processor, the processor being programmable and comprising means for sampling the first and second data channels at respective first and second sample rates, the first sample rate being greater than the second sample rate, the processor further comprising means for calculating and implementing first and second durations of first and second wake-up sessions, respectively, of the processor, the first duration of the first wake-up session being sufficient to permit the processor to sample data from the first channel only, the second duration being sufficient to permit the processor to sample data from the first and second channels, the processor further comprising means for powering up the processor for at least the first and second wake-up mode sessions and means for powering down the processor for at least first and second sleep mode sessions interposed, respectively, between the first and second wake-up mode sessions, and between the second and first wake-up sessions, comprising:

waking up the processor for the first wake-up mode session;

sampling data from the first channel only;

powering down the processor for the first sleep mode session;

waking up the processor for the second wake-up mode session;

sampling data from the first and second channels, and powering down the processor for the second sleep mode session.

2. The method of claim 1, wherein the first wake-up session and the second wake-up session occur at a predetermined time difference.

3. The method of claim 2, wherein the processor calculates the predetermined time difference by examining the number of channels to be sampled and the respective frequency at which each channel is to be sampled.

4. The method of claim 1, further comprising programming the processor with a number of channels to be sampled.

5. The method of claim 1, further comprising programming the processor with the respective frequencies at which each channel is to be sampled.

6. A battery-powered ambulatory medical data recorder, comprising:

a plurality of data channels connected to a plurality of corresponding medical sensors, including a first medical data sensor connected to a first data channel and a second medical data sensor connected to a second data channel;

a battery-powered processor, the processor being programmable and comprising means for sampling the first and second data channels at respective first and second sample rates, the first sample rate being greater than the second sample rate, the processor further comprising means for calculating and implementing first and second durations of first and second wake-up sessions, respectively, of the processor, the first duration of the first wake-up session being sufficient to permit the processor to sample data from the first channel only, the second duration being sufficient to permit the processor to sample data from the first and second channels, the processor further comprising means for powering up the processor for the first and second wake-up mode sessions and means for powering down the processor for at least a first sleep mode session interposed between the first and second wake-up mode sessions.

7. An ambulatory recorder according to claim 6, further comprising means for mounting the ambulatory recorder to a patient.

8. An ambulatory recorder according to claim 7, wherein the mounting means comprises a loop configured for a belt or a shoulder strap to be inserted therethrough.

9. An ambulatory recorder according to claim 6, wherein the first medical sensor comprises a pH sensing catheter.

10. An ambulatory medical data recorder, comprising:

first means for sampling a first data channel at a first programmed sample rate, the first data channel being connected to a first medical sensor;

second means for sampling a second data channel at a second programmed sample rate, the second data channel being connected to a second medical sensor;

means for programming the first sample rate;

means for programming the second sample rate;

means for determining the common time interval of shortest duration corresponding to the first sample rate and the second sample rate; and means for awakening the processor to first and second wake-up modes of at least first and second durations, respectively, the first and second durations corresponding to the first and second sample rates, respectively, the processor being awakened at a time interval defined by the shortest duration, the means for awakening further comprising means for maintaining the processor in the first wake-up mode for the first duration when the first data channel only is being sampled, and means for maintaining the processor in the second wakeup mode for the second duration when the first and second data channels are being sampled, the first duration being less than the second duration.

11. An ambulatory recorder according to claim 10, further comprising means for mounting the ambulatory recorder to a patient.

12. An ambulatory recorder according to claim 11, wherein the mounting means comprises a loop configured for a belt or a shoulder strap to be inserted therethrough.

13. An ambulatory recorder according to claim 10, wherein the first medical sensor comprises a pH sensing catheter.

* * * * *